United States Patent
IvanPetrov et al.

(10) Patent No.: US 9,612,205 B2
(45) Date of Patent: Apr. 4, 2017

(54) ETCHING AMOUNT MEASUREMENT APPARATUS FOR DRY ETCHING APPARATUS

(71) Applicant: Shibaura Mechatronics Corporation, Yokohama-shi, Kanagawa-ken (JP)

(72) Inventors: Ganachev IvanPetrov, Kanagawa (JP); Munenori Iwami, Kanagawa (JP)

(73) Assignee: SHIBAURA MECHATRONICS CORPORATION, Yokohama-Shi (JP)

( * ) Notice: Subject to any disclaimer, the term of this patent is extended or adjusted under 35 U.S.C. 154(b) by 11 days.

(21) Appl. No.: 14/463,947

(22) Filed: Aug. 20, 2014

(65) Prior Publication Data

US 2015/0062578 A1 Mar. 5, 2015

(30) Foreign Application Priority Data

Aug. 27, 2013 (JP) ................. 2013-175634

(51) Int. Cl.

| | |
|---|---|
| G01B 11/06 | (2006.01) |
| G01N 21/84 | (2006.01) |
| H01L 21/66 | (2006.01) |
| H01J 37/32 | (2006.01) |
| C09K 13/00 | (2006.01) |
| H01L 21/67 | (2006.01) |

(52) U.S. Cl.
CPC ........ G01N 21/84 (2013.01); H01J 37/32963 (2013.01); H01J 37/32972 (2013.01); H01L 22/12 (2013.01); H01L 22/26 (2013.01); H01L 22/30 (2013.01); C09K 13/00 (2013.01); G01B 2210/56 (2013.01); H01L 21/67253 (2013.01)

(58) Field of Classification Search
CPC ... H01L 22/12; H01L 22/16; H01L 21/67253; H01J 37/92963; H01J 37/32972
USPC ............... 356/630, 72, 326–330; 438/16
See application file for complete search history.

(56) References Cited

U.S. PATENT DOCUMENTS

| | | | |
|---|---|---|---|
| 5,244,527 A * | 9/1993 | Aoyagi ................. | B24B 37/013 156/345.16 |
| 2004/0087152 A1* | 5/2004 | Lian .................... | G01B 11/0675 438/689 |
| 2005/0088647 A1* | 4/2005 | Shanmugasundram | ........................... C23C 18/1651 356/72 |
| 2013/0157388 A1* | 6/2013 | Grimbergen ............ | H01L 22/12 438/9 |
| 2015/0012246 A1* | 1/2015 | Kim ....................... | G01B 11/06 702/172 |

FOREIGN PATENT DOCUMENTS

| | | |
|---|---|---|
| JP | 09-036090 A | 2/1997 |
| JP | 10-064884 A | 3/1998 |

* cited by examiner

*Primary Examiner* — Kara E Geisel
*Assistant Examiner* — Dominic J Bologna
(74) *Attorney, Agent, or Firm* — Pearne & Gordon LLP

(57) ABSTRACT

According to one embodiment, an etching amount measurement pattern is provided in a surface of a substrate. The pattern comprises a plurality of components two-dimensionally disposed and causing light incident on the pattern to be diffracted,
A configuration of the component has 4-fold rotational symmetry.
The plurality of components is arranged in a disposition having 4-fold rotational symmetry.

8 Claims, 3 Drawing Sheets

ETCHING AMOUNT MEASUREMENT APPARATUS FOR DRY ETCHING APPARATUS

CROSS-REFERENCE TO RELATED APPLICATIONS

This application is based upon and claims the benefit of priority from Japanese Patent Application No. 2013-175634, filed on Aug. 27, 2013; the entire contents of which are incorporated herein by reference.

BACKGROUND

Field

Embodiments described herein relate generally to an etching amount measurement pattern, etching amount measurement apparatus, and etching amount measurement method.

Description of the Related Art

In the manufacture of microstructures such as semiconductor devices, photomasks, etc., the end point of the plasma etching is detected from the change of the light emission spectrum of the plasma in the case where the etching object on which the plasma etching is to be performed includes multiple stacked layers (e.g., refer to JP-A H09-36090 (Kokai)).

However, in the case where the same material of the etching object is to be removed up to partway through the thickness, the end point detection cannot be performed based on the change of the light emission spectrum because the light emission spectrum of the plasma does not change.

Therefore, technology has been proposed in which light is irradiated on a measurement portion of the etching object where the processing end point is to be measured; and the thickness dimension (e.g., the film thickness) of the measurement portion is measured from the intensity change of coherent light (e.g., refer to JP-A H10-64884 (Kokai)).

That is, because the intensity of the coherent light and the thickness dimension of the measurement portion have a correlation, the thickness dimension of the measurement portion can be determined by sensing the intensity of the coherent light. Therefore, the fluctuation of the thickness dimension of the measurement portion during etching, that is, the etching amount, can be determined by successively sensing the intensity of the coherent light.

However, in the case where the thickness dimension of the measurement portion is determined using coherent light, problems occur because the upper limit of the measurable thickness dimension is small. In other words, in the case where the thickness dimension of the measurement portion is determined using coherent light, unfortunately, only components that are thin can be measured.

In such a case, generally, the measurement of the thickness dimension using coherent light is difficult unless the thickness dimension of the measurement portion is several tens times the wavelength of the light used in the measurement or less.

Therefore, for example, in the case where the thickness dimension of the measurement portion is 0.4 mm or more, there are cases where the measurement of the thickness dimension using coherent light and the measurement of the etching amount are difficult.

On the other hand, technology has been proposed in which the etching amount for a substrate having a thick measurement portion, etc., is measured from the light emission spectrum of light having a broad spectrum.

However, the polarization management in the wavelength range of the broad spectrum is complex. This is because the spectrum fluctuates according to the proportion of TE waves (Transverse Electric Waves) that have electric field components perpendicular to the incident direction and TM waves (Transverse Magnetic Waves) that have magnetic field components perpendicular to the incident direction.

Therefore, it is desirable to develop an etching amount measurement pattern for which the polarization management is unnecessary when measuring the etching amount using light having a broad spectrum.

SUMMARY

In general, according to one embodiment, an etching amount measurement pattern is provided in a surface of a substrate. The pattern comprises a plurality of components two-dimensionally disposed and causing light incident on the pattern to be diffracted, A configuration of the component has 4-fold rotational symmetry.

The plurality of components is arranged in a disposition having 4-fold rotational symmetry.

DETAILED DESCRIPTION

Figure 1:
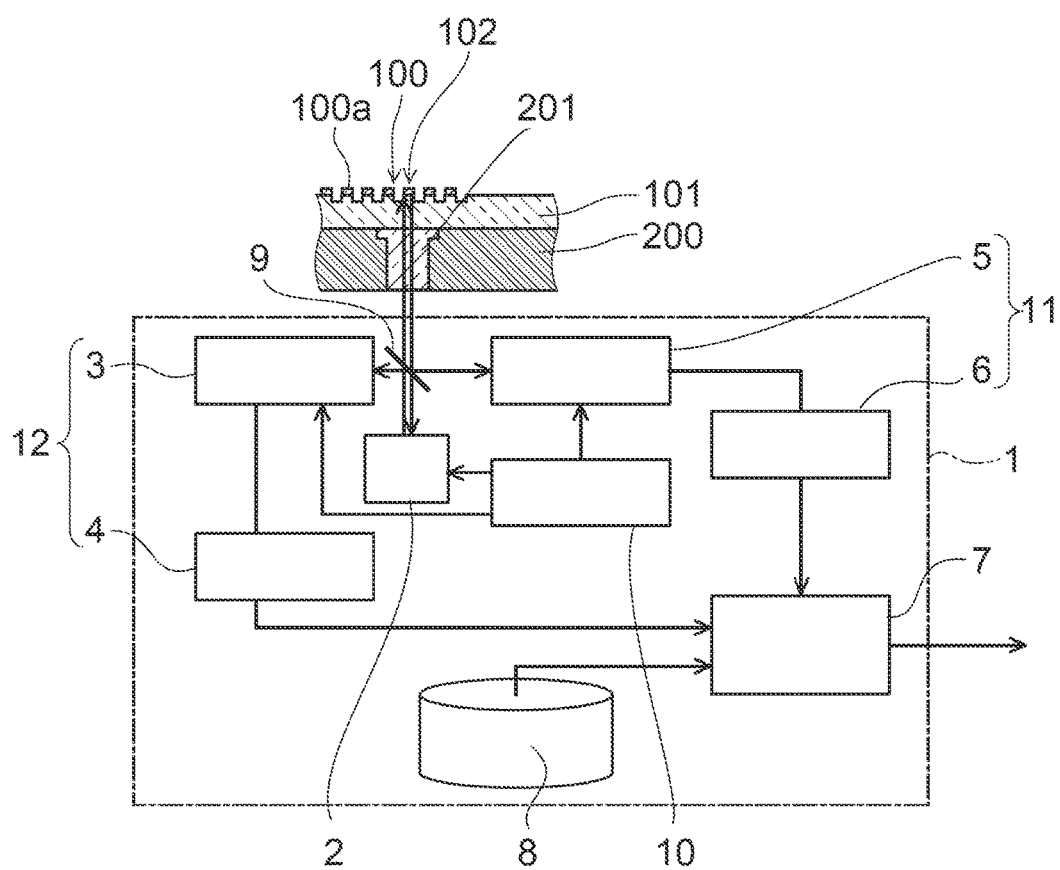
FIG. 1 is a schematic view showing an etching amount measurement apparatus 1 according to the embodiment.

Embodiments will now be described with reference to the drawings. Similar components in the drawings are marked with like reference numerals, and a detailed description is omitted as appropriate.

FIG. 1 is a schematic view showing an etching amount measurement apparatus 1 according to the embodiment. As shown in FIG. 1, a light source 2, a first spectral data generating unit 11, a second spectral data generating unit 12, a calculating unit 7, a data storage unit 8, a half mirror 9, and a control unit 10 are provided in the etching amount measurement apparatus 1.

The light source 2 irradiates light toward an etching amount measurement pattern 100 provided in the surface of a substrate 101.

In such a case, it is favorable for the light source 2 to be capable of irradiating light having a continuous spectral distribution. The light source 2 may be, for example, a xenon flash lamp, etc. If the light source 2 is a xenon flash lamp, the light source 2 can irradiate white light of a wide wavelength region of several hundred nm to one thousand and several hundred nm. Also, if the light source 2 is a xenon flash lamp, the light source 2 can irradiate white light in pulses.

The second spectral data generating unit 12 includes a spectrometer 3 and a compiler 4.

The second spectral data generating unit 12 generates second spectral data by separating the light irradiated from the light source 2. As described below, the second spectral data generating unit 12 may be omitted.

The spectrometer 3 separates the light that is irradiated from the light source 2 and incident via the half mirror 9 into each prescribed wavelength spectrum and performs a photoelectric conversion of the separated light spectra. The electrical signals for each of the separated light spectra are transmitted to the compiler 4. The spectrometer 3 may include, for example, a dispersive element such as a prism, a diffraction grating, etc., and a photoelectric conversion element such as a CCD (Charge Coupled Device), etc.

The compiler 4 generates the second spectral data by compiling the data of the intensity distribution for each light spectrum based on the electrical signals for each of the separated light spectra. The second spectral data that is generated is transmitted to the calculating unit 7.

The first spectral data generating unit 11 includes a spectrometer 5 and a compiler 6.

The first spectral data generating unit 11 generates the first spectral data by separating the diffracted light from a measurement portion 102 in which the etching amount measurement pattern 100 is provided.

The spectrometer 5 separates the light from the measurement portion 102 incident via the half mirror 9 for each prescribed wavelength spectrum and performs a photoelectric conversion of the separated light spectra. The electrical signals for each of the separated light spectra are transmitted to the compiler 6. The spectrometer 5 may include, for example, a dispersive element such as a prism, a diffraction grating, etc., and a photoelectric conversion element such as a CCD, etc.

The compiler 6 generates the first spectral data by compiling the data of the intensity distribution for each light spectrum based on the electrical signals for each of the separated light spectra. The first spectral data that is generated is transmitted to the calculating unit 7.

In the case where the second spectral data generating unit 12 is provided, the calculating unit 7 determines the return rate spectrum from the first spectral data and the second spectral data relating to the light irradiated from the light source 2. Then, the calculating unit 7 determines the etching amount of the measurement portion 102 from the determined return rate spectrum and a predetermined relationship between the return rate spectrum and the etching amount of the measurement portion 102.

In other words, first, the calculating unit 7 determines the return rate spectrum of the measurement portion 102 from the second spectral data generated by the compiler 4 and the first spectral data generated by the compiler 6.

As described below, the return rate of the light of the measurement portion 102 is the ratio of the intensity of the light (the diffracted light) from the measurement portion 102 in a prescribed direction (the case shown in FIG. 1, the direction perpendicular to the surface of the substrate 101) to the intensity of the light irradiated from the light source 2.

In other words, the return rate of the light of the measurement portion 102 can be expressed by the following formula: The return rate of the light of the measurement portion 102 equals the intensity of the light (the diffracted light) from the measurement portion 102 in a prescribed direction divided by the intensity of the light irradiated from the light source 2.

In the case where the substrate 101 is not transmissive to light of some of the wavelengths irradiated from the light source 2, the return rate of the light of the measurement portion 102 is determined from the light of wavelengths other than such wavelengths.

The details of the light from the measurement portion 102 being diffracted light are described below.

In such a case, the intensity of the light irradiated from the light source 2 may not be stable. Therefore, the second spectral data generating unit 12 (the spectrometer 3 and the compiler 4) is provided; the intensity of the light irradiated from the light source 2 is successively determined; and the return rate of the light of the measurement portion 102 is determined according to the fluctuation of the intensity of the light.

In such a case, when the fluctuation amount exceeds a prescribed value, the return rate of the light of the measurement portion 102 that is determined may not be employed.

If the intensity of the light irradiated from the light source 2 is stable, the return rate of the light of the measurement portion 102 can be determined based on a predetermined intensity of the light irradiated from the light source 2. Therefore, in the case where the intensity of the light irradiated from the light source 2 is stable, the second spectral data generating unit 12 (the spectrometer 3 and the compiler 4) may be omitted.

In such a case, the calculating unit 7 determines the etching amount of the measurement portion 102 from the first spectral data and a predetermined relationship between the first spectral data and the etching amount. In such a case, the first spectral data can be used as the return rate spectrum because the intensity of the light irradiated from the light source is stable and has a constant spectrum.

Then, the calculating unit 7 determines the relationship between the return rate of the light of the measurement portion 102 and the wavelength of the light, i.e., the return rate spectrum.

The return rate spectrum can be determined by determining the return rate of the light of each wavelength in the wavelength region of the light irradiated from the light source 2.

As described below, the return rate spectrum and the etching amount of the measurement portion 102 have a correlation.

Therefore, the calculating unit 7 then determines the etching amount of the measurement portion 102 using the return rate spectrum that is determined.

For example, the data relating to the predetermined relationship between the return rate spectrum and the etching amount of the measurement portion 102 is stored in the data storage unit 8. Then, the calculating unit 7 can determine the etching amount of the measurement portion 102 by comparing the return rate spectrum that is determined and the data that is provided from the data storage unit 8.

Also, the calculating unit 7 outputs the data relating to the etching amount of the measurement portion 102 that is determined.

For example, the data relating to the etching amount of the measurement portion 102 that is output may be displayed by a not-shown liquid crystal display device, etc., and/or used for the end point detection of the processing of a not-shown processing apparatus.

The data storage unit 8 stores the data relating to the predetermined relationship between the return rate spectrum and the etching amount of the measurement portion 102.

The data relating to the relationship between the return rate spectrum and the etching amount of the measurement portion 102 may be predetermined by, for example, performing experiments and/or simulations.

The details relating to the relationship between the return rate spectrum and the etching amount of the measurement portion 102 are described below.

The half mirror 9 reflects a portion of the light irradiated from the light source 2 and causes the portion of the light to be incident on the spectrometer 3. The light that is irradiated from the light source 2 and passes through the half mirror 9 is irradiated on the measurement portion 102. Also, the half mirror 9 reflects a portion of the light from the measurement portion 102 and causes the portion of the light to be incident on the spectrometer 5.

The control unit 10 controls the operations of the components provided in the etching amount measurement apparatus 1. The control unit 10 controls, for example, the operations of the light source 2, the spectrometer 3, and the spectrometer 5.

The etching amount measurement pattern 100 will now be described.

The etching amount measurement pattern 100 is provided in the surface of the substrate 101 which is the etching object. The substrate 101 is formed from a material that can transmit the light irradiated from the light source 2. However, it is unnecessary for the substrate 101 to be transmissive to light of all of the wavelengths irradiated from the light source 2; and it is sufficient to be transmissive to, for example, light of some of the wavelengths irradiated from the light source 2.

Here, the thickness dimension of the substrate 101 can be determined by sensing the intensity of the coherent light produced by the light that is reflected at one major surface of the substrate 101 and the light that enters the interior of the substrate 101 from the one major surface of the substrate 101 and is reflected at the major surface on the opposite side. That is, because the intensity of the coherent light and the thickness dimension of the substrate 101 have a correlation, the thickness dimension of the substrate 101 can be determined by sensing the intensity of the coherent light. Therefore, if the intensity of the coherent light is successively sensed, for example, the fluctuation of the thickness dimension of the measurement portion during etching, i.e., the etching amount, can be determined.

However, in the case where the thickness dimension of the measurement portion is determined using coherent light, problems occur because the upper limit of the measurable thickness dimension is small. In other words, in the case where the thickness dimension of the measurement portion is determined using coherent light, unfortunately, only components that are thin can be measured. That is, the measurement of the thickness dimension using coherent light is affected by the wavelength of the light used in the measurement, the refractive index of the measurement object, the resolution of the optical system of the spectrometer, etc.; and the separation of the reflected light becomes difficult as the thickness dimension of the measurement portion increases. Therefore, the measurement of the thickness dimension using coherent light becomes difficult as the thickness dimension of the measurement portion increases.

In such a case, generally, the measurement of the thickness dimension using coherent light is difficult unless the thickness dimension of the measurement portion is several tens times the wavelength of the light used in the measurement or less.

Therefore, for example, when the thickness dimension of the measurement portion is 0.4 mm or more, there are cases where the measurement of the thickness dimension using coherent light and the measurement of the etching amount are difficult.

On the other hand, there is known technology that measures the etching amount for a thick substrate, etc., from the light emission spectrum of light having a broad spectrum.

However, the polarization management in the wavelength range of the broad spectrum is complex.

Therefore, the etching amount measurement pattern 100 according to the embodiment can produce diffracted light. Then, as described below, the etching amount of the measurement portion 102 is measured using the diffracted light.

If the etching amount of the measurement portion 102 is measured using the diffracted light, the etching amount of the measurement portion 102 can be determined with high precision even in the case where the thickness dimension of the measurement portion is thick (e.g., even in the case where the thickness dimension of the measurement portion is 0.4 mm or more).

To produce the diffracted light, the etching amount measurement pattern 100 functions as a diffraction grating.

Further, the etching amount measurement pattern 100 is not easily affected by polarization.

Therefore, by using the etching amount measurement pattern 100 according to the embodiment, the polarization management is unnecessary when measuring the etching amount using light having a broad spectrum.

The effects of polarization for the etching amount measurement pattern 100 are described below.

Figure 2A:
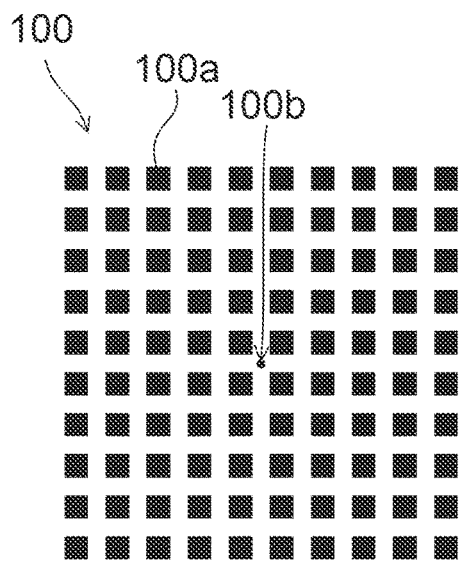
FIGS. 2A, 2B, and 2C are schematic views showing the etching amount measurement pattern 100.
Figure 2B:
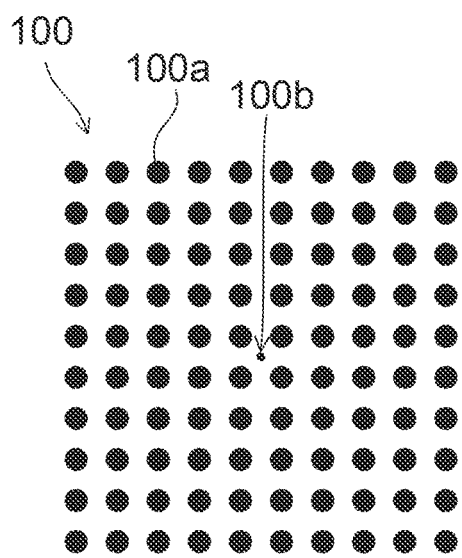
Figure 2C:
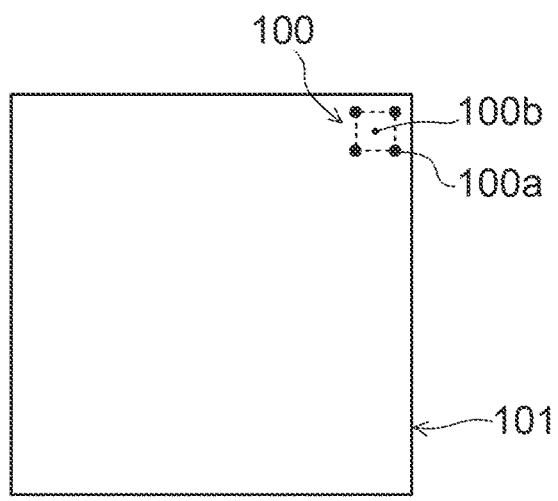

FIGS. 2A, 2B, and 2C are schematic views showing the etching amount measurement pattern 100.

As shown in FIGS. 2A, 2B, and 2C, the etching amount measurement pattern 100 is provided in the surface of the substrate 101, includes multiple components 100a that are two-dimensionally disposed, and diffracts the light that is incident. The component 100a has a configuration having 4-fold rotational symmetry and is multiply provided in the etching amount measurement pattern 100. In other words, the component 100a has a configuration that, when rotated 90° around the center of the component 100a, overlaps the configuration prior to the rotation. For example, the component 100a shown in FIG. 2A is a square; and the component 100a shown in FIG. 2B is a circle.

Further, the multiple components 100a are arranged in the etching amount measurement pattern 100 in a disposition having 4-fold rotational symmetry. In other words, the multiple components 100a, when rotated 90° around a center 100b of the etching amount measurement pattern 100, have a disposition that overlaps the disposition prior to the rotation. For example, in the etching amount measurement pattern 100 shown in FIGS. 2A and 2B, the multiple components 100a are arranged in 10 rows by 10 columns at uniform pitch dimensions.

Because the etching amount measurement pattern 100 includes the multiple components 100a that have configurations having 4-fold rotational symmetry and are arranged in a disposition having 4-fold rotational symmetry, similar return rate spectra can be obtained for TE waves and TM waves of which the directions of the electric field components are different by 90°.

Therefore, similar return rate spectra can be obtained regardless of the proportion of the TE waves and the TM waves for the light irradiated from the light source 2.

In other words, high-precision measurement of the etching amount can be performed even in the case where the etching amount measurement pattern 100 is fine because the effects of polarization can be suppressed.

The pitch dimension, external dimension, configuration, number, etc., of the component 100a are not limited to those described above and may be modified appropriately.

However, by considering the wavelength of the light irradiated from the light source 2, it is necessary for the pitch dimension of the components 100a to be such that the components 100a function as a diffraction grating.

If the etching amount measurement pattern 100 functions as a diffraction grating, the light that is incident on the measurement portion 102 and returns to the light source 2 side can be diffracted light.

Unlike light traveling in straight lines and reflected light which propagate in directions of geometrical propagation, diffracted light propagates by traveling through regions where geometrical propagation is not possible. Therefore, diffracted light propagates in multiple directions.

Here, for diffracted light, there is a correlation between the energy of the light (the intensity of the light) propagating in each direction and the size (the etching amount) of the unevenness of the incident surface of the light. Therefore, the etching amount of the measurement portion 102 can be determined by determining the return rate spectrum of the light in a prescribed propagation direction.

For example, the direction in which the diffracted light disperses changes as the surface configuration of the measurement portion 102 changes due to the etching. Therefore, the surface configuration can be measured by measuring the spectrum of the diffracted light (the return rate spectrum of the light) in the prescribed propagation direction. Here, for the surface configuration, the dimensions (e.g., the dimension between the components 100a and the pitch dimension of the components 100a) other than the depth dimension (the etching dimension) between the components 100a of the measurement pattern 100 do not change as the etching progresses; but the depth dimension between the components 100a changes. Accordingly, the depth dimension between the components 100a, i.e., the etching amount, can be measured by measuring the surface configuration.

Conversely, the reflected light and the light traveling in straight lines which propagate in directions of geometrical propagation propagate in prescribed directions. Therefore, the reflected light and the light traveling in straight lines do not propagate in multiple directions; and the light energy propagating in each direction does not change according to the size of the unevenness of the incident surface of the light. Therefore, the etching amount of the measurement portion 102 cannot be determined using the reflected light and the light traveling in straight lines.

However, according to knowledge obtained by the inventors, it was ascertained that the return rate spectrum fluctuates due to the effects of polarization in the case where the etching amount measurement pattern 100 is fine.

For example, light can be considered to be the superimposition of TE waves (Transverse Electric Waves) that have electric field components perpendicular to the incident direction and TM waves (Transverse Magnetic Waves) that have magnetic field components perpendicular to the incident direction.

It was ascertained that the return rate spectrum of the measurement portion 102 fluctuates according to the proportion of the TE waves and the TM waves when the etching amount measurement pattern 100 is fine.

Figure 3:
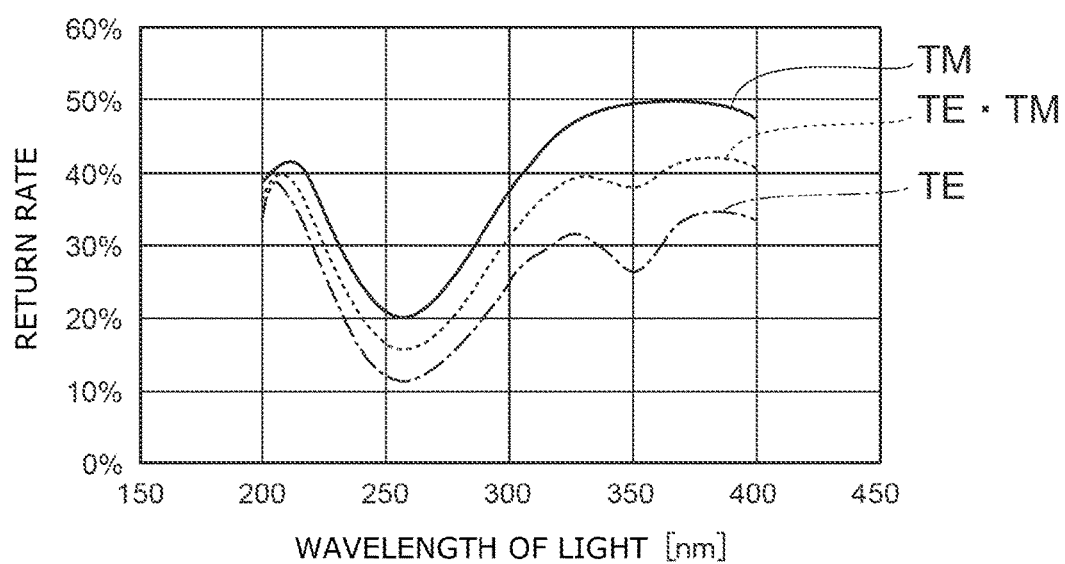
FIG. 3 is a graph of the fluctuation of the return rate spectrum of the measurement portion 102 according to the proportion of the TE waves and the TM waves.

FIG. 3 is a graph of the fluctuation of the return rate spectrum of the measurement portion 102 according to the proportion of the TE waves and the TM waves.

In FIG. 3, TE is the case where the proportion of the TE waves is 100%. TM is the case where the proportion of the TM waves is 100%. TE·TM is the case where the proportions of the TE waves and the TM waves are 50% each.

The etching amount measurement pattern is a line & space pattern having a width dimension of the space portion of 300 nm and a pitch dimension of the space portion of 300 nm.

In this case, the material of the substrate 101 is quartz. In this case, the thickness dimension of the substrate 101 is 2 mm; and the depth dimension (the etching amount) of the recess at the space portion is 170 nm.

FIG. 3 shows the results determined by performing a simulation using the conditions described above.

It can be seen from FIG. 3 that even for the same etching amount, the return rate spectrum fluctuates as the proportion of the TE waves and the TM waves changes.

In such a case, the light irradiated from the light source 2 has various proportions of TE waves and TM waves. Therefore, the etching amount of the measurement portion 102 cannot be determined simply by providing a pattern (e.g., a line & space pattern) that functions as a diffraction grating.

Here, even in the case of, for example, a line & space pattern, etc., the etching amount of the measurement portion 102 can be determined by controlling the polarization using a polarizing filter, etc.

However, it is difficult to obtain a polarizing filter or the like that is capable of accommodating a wide wavelength region. Moreover, if a polarizing filter or the like that is capable of accommodating a wide wavelength region is used, the cost of the etching amount measurement apparatus 1 increases.

Therefore, the etching amount measurement pattern 100 according to the embodiment functions as a diffraction grating and is not affected easily by the polarization.

As described above, the diffracted light that is from the measurement portion 102 in which the etching amount measurement pattern 100 is provided propagates in multiple directions. The directions in which the diffracted light propagates can be represented by the diffraction peak angle, the diffraction peak direction, the diffraction angle, etc.

In such a case, it is favorable to use the intensity of the light propagating in a direction perpendicular to the surface of the substrate 101 when determining the etching amount of the measurement portion 102.

However, in the case where the diffraction angles are near each other, it becomes difficult to separate the light propagating in directions perpendicular to the surface of the substrate 101. Therefore, the etching amount of the measurement portion 102 may be difficult to determine.

Here, the diffraction angles are proportional to the ratio of the wavelength of the light to the pitch dimension of the components 100a; and the angle between the diffraction angles is inversely proportional to the ratio of the wavelength of the light to the pitch dimension of the components 100a. To make the light propagating in directions perpendicular to the surface of the substrate 101 easy to separate, it is favorable for the angle between the diffraction angles to be larger than the resolution of the spectrometer 5.

To make the angle between the diffraction angles larger than the resolution of the spectrometer 5, it is sufficient to set the pitch dimension of the components 100a to be small.

In such a case, if the pitch dimension of the components 100a is set to be the shortest wavelength of the light irradiated from the light source 2 divided by the numerical aperture of the spectrometer 5 or less, the light that propagates in directions perpendicular to the surface of the substrate 101 is easily incident on the spectrometer 5.

For example, if the pitch dimension of the components 100a is set to be 50 times the shortest wavelength of the light irradiated from the light source 2 or less, the light that propagates in directions perpendicular to the surface of the substrate 101 is easily incident on the spectrometer 5.

The external dimensions of the component 100a are not particularly limited. However, by considering the pitch dimension of the components 100a, it is favorable for the external dimensions of the component 100a to be such that the dimension between the components 100a is about the same as the dimension of the trench portion of the microstructure (the pattern dimension of the product) formed in the surface of the substrate 101.

In such a case, it is favorable for the total surface area of the multiple components 100a to be the same as the surface area between the multiple components 100a.

Thus, the etching amount of the measurement portion 102 can be determined easily because the contrast can be high.

As long as the configuration of the component 100a has 4-fold rotational symmetry, the configuration is not particularly limited. For example, the configuration of the component 100a may be a cross-shaped configuration, etc.

However, the formation of the etching amount measurement pattern 100 is easy when the configuration of the component 100a is a square.

As long as the transmission of the light irradiated from the light source 2 can be suppressed, the material of the component 100a is not particularly limited.

However, it is favorable for the material of the component 100a to be resistant to the etching.

The material of the component 100a may be, for example, a metal such as chrome, etc.

The thickness dimension of the component 100a is not particularly limited. However, in the case where the thickness dimension of the component 100a is too thin, there is a risk that the configuration, pitch dimension, etc., of the component 100a may change in the etching and it may be difficult to measure the etching amount of the measurement portion 102. Therefore, it is favorable to set the thickness dimension of the component 100a by considering the resistance of the material to the etching, etc.

The disposition position of the etching amount measurement pattern 100 in the surface of the substrate 101 is not particularly limited. In this case, the etching amount measurement pattern 100 may be provided in a region other than the region where the microstructure is formed (e.g., the region where the circuit pattern of the product and the like are formed, etc.) in the surface of the substrate 101. For example, as shown in FIG. 2C, the etching amount measurement pattern 100 may be provided in the circumferential edge vicinity of the substrate 101.

In the case where the etching rate has a distribution in the surface, it is favorable to correct the etching amount of the measurement portion 102 that is measured based on a predetermined distribution in the surface of the etching rate.

The distribution in the surface of the etching rate may be predetermined by performing experiments, simulations, etc.

In such a case, the data relating to the predetermined distribution in the surface of the etching rate may be stored in the data storage unit 8. Then, the calculating unit 7 can correct the etching amount of the measurement portion 102 using the data relating to the distribution in the surface of the etching rate that is stored in the data storage unit 8.

Effects of the etching amount measurement apparatus 1 and an etching amount measurement method according to the embodiment will now be described.

First, the substrate 101 in which the etching amount measurement pattern 100 is provided is transferred into the interior of a not-shown processing apparatus by a not-shown transfer apparatus, etc.

A not-shown mask for forming the pattern of the product is provided on the surface of the substrate 101.

The substrate 101 that is transferred into the interior of the not-shown processing apparatus is placed on a placement platform 200 that has a transmissive window 201 that transmits light.

The transmissive window 201 is provided at a position that faces the etching amount measurement pattern 100.

The not-shown processing apparatus may include, for example, a dry etching apparatus such as a plasma etching apparatus, etc.

Then, processing of the substrate 101 is performed by the not-shown processing apparatus.

For example, plasma products such as neutral active species, ions, etc., are produced by exciting and activating a prescribed gas by generating plasma in the interior of the not-shown processing apparatus.

Then, the pattern of the product is formed by etching the surface of the substrate 101 not covered with the not-shown mask by using the plasma products that are produced.

At this time, the etching amount of the measurement portion 102 is determined by the etching amount measurement apparatus 1 as follows.

First, light of a prescribed wavelength region is irradiated from the light source 2 toward the measurement portion 102 in which the etching amount measurement pattern 100 is provided.

As described above, in the case where the second spectral data generating unit is provided, a portion of the light irradiated from the light source 2 is incident on the spectrometer 3 via the half mirror 9.

The spectrometer 3 separates the light that is incident for each prescribed wavelength spectrum and performs photoelectric conversion. The compiler 4 generates the second spectral data based on the electrical signals for each of the separated light spectra.

A portion of the light from the measurement portion 102 is incident on the spectrometer 5 via the half mirror 9. The spectrometer 5 separates the light that is incident for each prescribed wavelength spectrum and performs photoelectric conversion. The compiler 6 generates the first spectral data based on the electrical signals for each of the separated light spectra.

First, the calculating unit 7 determines the return rate spectrum.

For example, the calculating unit 7 determines the return rate spectrum by determining the light of each wavelength in the wavelength region of the light irradiated from the light source 2.

In the case where the second spectral data generating unit is not provided, the calculating unit 7 determines the etching amount of the measurement portion 102 from the first spectral data and a predetermined relationship between the first spectral data and the etching amount.

In such a case, the first spectral data can be used as the return rate spectrum because the intensity of the light irradiated from the light source is stable and has a constant spectrum.

Then, the calculating unit 7 determines the etching amount of the measurement portion 102 using the return rate spectrum that is determined.

For example, the calculating unit 7 determines the etching amount of the measurement portion 102 by comparing the return rate spectrum that is determined and the data relating to the predetermined relationship between the return rate spectrum and the etching amount of the measurement portion 102.

The calculating unit 7 outputs the data relating to the etching amount of the measurement portion 102 that is determined.

For example, the data relating to the etching amount of the measurement portion 102 that is output is displayed by a not-shown liquid crystal display device, etc., and/or used for the end point detection of the processing of a not-shown processing apparatus.

In other words, the etching amount measurement method according to the embodiment may include the following processes.

(1) A process of irradiating light toward the etching amount measurement pattern 100 provided in the surface of the substrate 101.

(2) A process of generating the first spectral data by separating the diffracted light from the measurement portion 102 in which the etching amount measurement pattern 100 is provided.

(3) A process of determining the etching amount of the measurement portion from the first spectral data and a predetermined relationship between the first spectral data and the etching amount.

The embodiments have been illustrated above. However, the invention is not limited to these descriptions.

Those skilled in the art can suitably modify the above embodiments by addition, deletion, or design change of components, or by addition, omission, or condition change of processes, and such modifications are also encompassed within the scope of the invention as long as they fall within the spirit of the invention.

What is claimed is:

1. An etching amount measurement apparatus for a dry etching apparatus, comprising:
   a placement platform on which a substrate is mounted, the substrate having a first surface and a second surface, an etching amount measurement pattern being provided in the second surface of the substrate, the pattern functioning as a diffraction grating;
   a transmissive window being provided at a position that faces the pattern;
   a light source irradiating light to the first surface of the substrate through the window, light irradiated to the first surface propagating through an inside of the substrate, said propagating light being incident to the pattern and diffracted by the pattern, said diffracted light propagating through the inside of the substrate, said propagating light being irradiated outside from the first surface;
   a first spectral data generating unit generating first spectral data by separating diffracted light from a measurement portion, the pattern being provided in the measurement portion; and
   a calculating unit determining an etching amount of the measurement portion from the first spectral data and a relationship between the first spectral data and the etching amount, the relationship being predetermined;
   the pattern comprising a plurality of components, a configuration of the component having 4-fold rotational symmetry, the plurality of components being arranged in a disposition having 4-fold rotational symmetry, the plurality of components being formed from a material that inhibits the transmission of incident light, and the substrate being formed from a material that can transmit incident light.

2. The apparatus according to claim 1, further comprising a data storage unit storing data relating to the predetermined relationship between the etching amount of the measurement portion and the first spectral data.

3. The apparatus according to claim 1, wherein the configuration of the component is a square.

4. The apparatus according to claim 1, wherein the total surface area of the plurality of components is the same as the surface area between the plurality of components.

5. The apparatus according to claim 1, the plurality of components include chrome.

6. An etching amount measurement method performed by the apparatus according to claim 1, comprising the steps of:
   irradiating, by the light source, light toward the pattern;
   generating, by the first spectral data generating unit, the first spectral data by separating diffracted light from the measurement portion, the pattern being provided in the measurement portion; and
   determining, by the calculating unit, the etching amount of the measurement portion.

7. An etching amount measurement apparatus for a dry etching apparatus, comprising:
   a placement platform on which a substrate is mounted, the substrate having a first surface and a second surface, an etching amount measurement pattern being provided in the second surface of the substrate, the pattern functioning as a diffraction grating;
   a transmissive window being provided at a position that faces the pattern;
   a light source irradiating light to the first surface of the substrate through the window, light irradiated to the first surface propagating through an inside of the substrate, said propagating light being incident to the pattern and diffracted by the pattern, said diffracted light propagating through the inside of the substrate, said propagating light being irradiated outside from the first surface;
   a first spectral data generating unit generating first spectral data by separating diffracted light from a measurement portion, the pattern being provided in the measurement portion;
   a second spectral data generating unit generating second spectral data relating to the light irradiated from the light source by separating the light irradiated from the light source; and
   a calculating unit determining a return rate spectrum from the first spectral data and the second spectral data and determining an etching amount of the measurement portion from the determined return rate spectrum and a relationship between the return rate spectrum and the etching amount of the measurement portion, the relationship being predetermined;
   the pattern comprising a plurality of components, a configuration of the component having 4-fold rotational symmetry, the plurality of components being arranged in a disposition having 4-fold rotational symmetry, the plurality of components being formed from a material that inhibits the transmission of incident light, and the substrate being formed from a material that can transmit incident light.

8. The apparatus according to claim 7, further comprising a data storage unit storing data relating to the predetermined relationship between the etching amount of the measurement portion and the first spectral data or the return rate spectrum.

* * * * *